United States Patent
Bokrantz et al.

(10) Patent No.: US 11,865,363 B2
(45) Date of Patent: Jan. 9, 2024

(54) METHOD AND A CORRESPONDING RADIATION TREATMENT SYSTEM FOR FACILITATING OPTIMIZATION OF A MULTIMODAL RADIATION THERAPY PLAN

(71) Applicant: RaySearch Laboratories AB, Stockholm (SE)

(72) Inventors: Rasmus Bokrantz, Stockholm (SE); Albin Fredriksson, Stockholm (SE); Kjell Eriksson, Bålsta (SE); Erik Engwall, Hägersten (SE); Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 584 days.

(21) Appl. No.: 17/057,170

(22) PCT Filed: May 27, 2019

(86) PCT No.: PCT/EP2019/063676
§ 371 (c)(1),
(2) Date: Nov. 20, 2020

(87) PCT Pub. No.: WO2019/228997
PCT Pub. Date: Dec. 5, 2019

(65) Prior Publication Data
US 2021/0205635 A1    Jul. 8, 2021

(30) Foreign Application Priority Data
May 30, 2018    (EP) ..................................... 18175043

(51) Int. Cl.
*A61N 5/10*    (2006.01)

(52) U.S. Cl.
CPC .... *A61N 5/1031* (2013.01); *A61N 2005/1089* (2013.01); *A61N 2005/1091* (2013.01)

(58) Field of Classification Search
CPC .......... A61N 5/1031; A61N 2005/1089; A61N 2005/1091; A61N 5/10
See application file for complete search history.

(56) References Cited

U.S. PATENT DOCUMENTS 6,714,620 B2 *   3/2004   Caflisch ................. A61N 5/103
                                                            378/65
2006/0033044 A1   2/2006   Gentry et al.
(Continued)

FOREIGN PATENT DOCUMENTS

CN    102939607 A    2/2013
CN    107666940 A    2/2018
(Continued)

OTHER PUBLICATIONS

First Examination Report dated Aug. 8, 2022 in Indian Patent Application No. 202017047300 (with English translation).
(Continued)

*Primary Examiner* — Kiho Kim
(74) *Attorney, Agent, or Firm* — Faegre Drinker Biddle & Reath LLP (57) ABSTRACT

The present disclosure generally relates to the field of radiation treatment. More specifically, the present disclosure generally relates to methods and radiation treatment systems for facilitating a multimodal radiation therapy treatment plan, in particular a multimodal radiation therapy plan employing a combined photon beam and electron beam radiation treatment. According to one example embodiment described in the disclosure, a method may comprise obtaining information related to a set of candidate beam types for the combined photon beam and electron beam radiation treatment; comparing the set of candidate beam types
(Continued)

against a selection criterion to establish a subset of beam types from the candidate beam types; and generating the combined photon beam and electron beam radiation treatment plan utilizing the thus established subset of beam types.

9 Claims, 4 Drawing Sheets

(56) References Cited

U.S. PATENT DOCUMENTS

| | | |
|---|---|---|
| 2013/0090549 A1 | 4/2013 | Meltsner et al. |
| 2016/0254121 A1 | 9/2016 | Amir |
| 2016/0331997 A1 | 11/2016 | Vilsmeier |

FOREIGN PATENT DOCUMENTS

| | | |
|---|---|---|
| DE | 10 2015 209 809 A1 | 3/2016 |
| JP | 2018-502655 A | 2/2018 |
| WO | WO-00/15299 A1 | 3/2000 |
| WO | WO-2016/188754 A1 | 12/2016 |
| WO | WO-2018/053648 A1 | 3/2018 |

OTHER PUBLICATIONS

Chinese Office Action dated Mar. 4, 2023 in Chinese Patent Application No. 201980035142.2.

Japanese Office Action dated Apr. 25, 2023 in Application No. 2020-566661.

* cited by examiner

METHOD AND A CORRESPONDING RADIATION TREATMENT SYSTEM FOR FACILITATING OPTIMIZATION OF A MULTIMODAL RADIATION THERAPY PLAN

This application is the National Stage of International Application No. PCT/EP2019/063676, filed May 27, 2019, and claims benefit of European Patent Application No. 18175043.1, filed May 30, 2018, the entire contents of which are incorporated by reference herein.

TECHNICAL FIELD

The present disclosure generally relates to the field of radiation treatment. More specifically, the present disclosure generally relates to methods and radiation treatment systems for facilitating a multimodal radiation therapy treatment plan, in particular a multimodal radiation therapy plan employing a combined photon beam and electron beam radiation treatment. As will be appreciated, the various aspects and embodiments described herein therefore find particular utility in multimodal radiotherapy planning optimization procedures and systems, where the multimodal radiation therapy plan employs a combined photon beam and electron beam radiation treatment.

BACKGROUND

Optimization algorithms for external beam radiotherapy have existed for some time. However, cancer treatment centers are incorporating more types of radiation modalities into the planning process as they become increasingly available. For example, a cancer treatment site may combine photon and electron based beam therapies into one prescription for cancer patients. Such combination therapies typically utilize separate algorithms for optimizing the dose given to the patient for each type of modality. These algorithms may be inherently inadequate, because the optimization regimes are not inclusive of all treatment types simultaneously.

In traditional radiation therapy planning algorithms, it is sometimes attempted to create a set of radiation beam shapes and weights to satisfy user-defined objectives. These objectives may for example include minimum, maximum, uniform, etc., dose to the target cancer site and/or surrounding organs. These radiation therapy planning algorithms typically utilize only one treatment modality at a time. However, as described above, more and more cancer centers have gained access to different treatment modalities. Currently, there are radiation therapy devices that deliver photons of radiation and other radiation therapy devices that deliver electrons. As is known among persons skilled in the art of radiation therapy planning systems, each one has its own pros and cons and although there exist appropriate dose optimization programs for each one, such programs typically optimize the dose of only one of these modalities exclusively.

WO 2018/053648 A1 was cited in. EP18175043.1. WO 2018/053648 A1 relates in general to treatment planning based on multiple modalities.

SUMMARY

It is in view of the above considerations and others that the various aspects and embodiments disclosed herein have been made.

Despite the advances in radiation treatment technology for cancer treatment, the present disclosure recognizes the fact that there is still an unmet need for radiation treatment systems and methods that facilitate using a single combined optimization technique for multimodal radiation therapy planning employing a combined photon beam and electron beam radiation treatment. In contrast to WO 2018/053648 A1 which focuses on multiple modalities in general, this disclosure is exclusively focused on multimodal radiation therapy planning employing a combined photon beam and electron beam radiation treatment.

In view of the above, it is therefore a general object of the aspects and embodiments described throughout this disclosure to provide a solution, which overcomes one or more of the deficiencies noted hereinabove. More particularly, the various aspects and embodiments address the object of facilitating a multimodal radiation therapy plan employing a combined photon beam and electron beam radiation treatment.

The above-identified general object has been addressed by the appended independent claims. Advantageous embodiments are defined in the appended dependent claims.

According to a first aspect, this disclosure presents a method of facilitating optimization of a multimodal radiation therapy plan employing a combined photon beam and electron beam radiation treatment. Information related to a set of candidate beam types for the combined photon beam and electron beam radiation treatment is obtained. Each candidate beam type of the set of candidate beam types may include one or more beam type parameters. Furthermore, the set of candidate beam types is compared against a selection criterion to establish a subset of beam types from the candidate beam types. Still further, the combined photon beam and electron beam radiation treatment plan is generated, or otherwise created, utilizing only the established subset of beam types.

In advantageous embodiments, the method additionally comprises concurrently optimizing a dose delivery from a photon therapy device and an electron therapy device applying the generated combined photon beam and electron beam radiation treatment plan. In some embodiments, the photon therapy device and an electron therapy device may be separate devices. That is, the photon therapy device and the electron therapy device may be separate and distinct from each other. However, in alternative preferred embodiments, the photon therapy device and the electron therapy device are implemented into one single apparatus. Sometimes the single apparatus may then be referred to as a photon-electron therapy apparatus.

In some embodiments, the above-mentioned selection criterion imposes a requirement such that only a limited number of beam types qualify as the subset of beam types for subsequent utilization in the combined photon beam and electron beam radiation treatment plan utilizing only the established subset of beam types.

Furthermore, the earlier-mentioned beam type parameter may include one or more of the following: beam energy; beam modality; beam trajectory; dose per unit of time; distance to volume of interest; beam placement on or within volume of interest; beam modifiers such as multileaf collimator, jaws, wedges, blocks, scattering foil, compensator, cutout and bolus; and machine characteristics.

In advantageous embodiments, the method may additionally comprise acquiring an image (e.g., by means of a scanner) of a volume of interest to be treated using the combined photon beam and electron beam radiation treatment plan, converting the acquired image into image data;

and evaluating the image data. The earlier-mentioned selection criterion may be determined or otherwise established on the basis of the evaluation of the image data.

According to a second aspect, this disclosure presents a radiation treatment system that facilitates optimization a multimodal radiation therapy plan employing a combined photon beam and electron beam radiation treatment. The radiation treatment system comprises at least one processor and at least one memory. The at least one memory comprises instructions executable by the at least one processor whereby the radiation treatment system is operative to i) obtain information related to a set of candidate beam types for the combined photon beam and electron beam radiation treatment, each candidate beam type of the set of candidate beam types including one or more beam type parameters, ii) compare the set of candidate beam types against a selection criterion to establish a subset of beam types from the candidate beam types; and iii) generate or otherwise create the combined photon beam and electron beam radiation treatment plan utilizing only the established subset of beam types.

Advantageously, the at least one memory may also comprise instructions executable by the at least one processor whereby the radiation treatment system is operative to concurrently optimize a dose delivery from a photon therapy device and an electron therapy device applying the generated combined photon beam and electron beam radiation treatment plan. That is, the photon therapy device and the electron therapy device may be separate and distinct from each other. However, in alternative preferred embodiments, the photon therapy device and the electron therapy device are implemented into one single apparatus. Sometimes the single apparatus may then be referred to as a photon-electron therapy apparatus.

In some embodiments, the earlier-mentioned selection criterion imposes a requirement such that only a limited number of beam types qualify as the subset of beam types for subsequent utilization in the combined photon beam and electron beam radiation treatment plan utilizing only the established subset of beam types.

The above-mentioned beam type parameter may include one or more of the following: beam modality; beam trajectory; dose per unit of time; distance to volume of interest; beam placement on or within volume of interest; beam modifiers such as multileaf collimator, jaws, wedges, blocks, scattering foil, compensator, cutout and bolus; and machine characteristics.

Additionally, in some embodiments the at least one memory may comprise instructions executable by the at least one processor whereby the radiation treatment system is operative to acquire (e.g., by means of a scanner) an image of a volume of interest to be treated using the combined photon beam and electron beam radiation treatment plan; convert the acquired image into image data; evaluate the image data; and determine said selection criterion on the basis of the evaluation of the image data.

According to a third aspect, this disclosure presents this disclosure presents computer program, comprising instructions which, when executed on at least one processor, cause the at least one processor to carry out the method according to the earlier-described first aspect.

A carrier comprising the computer program according the third aspect may also optionally be provided. The carrier may, e.g., be an electronic signal, an optical signal, a radio signal or a computer-readable storage medium.

For example, a computer-readable medium may have stored thereon one or more sequences of instructions for causing one or more processors to perform: obtaining information related to a set of candidate beam types for the combined photon beam and electron beam radiation treatment, each candidate beam type of the set of candidate beam types including one or more beam type parameters; comparing the set of candidate beam types against a selection criterion to establish a subset of beam types from the candidate beam types; and generating or otherwise creating the combined photon beam and electron beam radiation treatment plan utilizing only the established subset of beam types.

Advantageously, the computer-readable medium may additional have stored thereon one or more sequences of instructions for causing one or more processors to perform concurrently optimizing a dose delivery from a photon therapy device and an electron therapy device applying the generated combined photon beam and electron beam radiation treatment plan.

The above-mentioned selection criterion may impose a requirement such that only a limited number of beam types qualify as the subset of beam types for subsequent utilization in the combined photon beam and electron beam radiation treatment plan utilizing only the established subset of beam types.

The earlier-mentioned beam type parameter may for example include one or more of the following: beam modality; beam trajectory; dose per unit of time; distance to volume of interest; beam placement on or within volume of interest; beam modifiers such as multileaf collimator, jaws, wedges, blocks, scattering foil, compensator, cutout and bolus; and machine characteristics.

Additionally, in some advantageous embodiments the computer-readable medium may have stored thereon one or more sequences of instructions for causing one or more processors to perform evaluating image data representing an acquired image of a volume of interest to be treated using the combined photon beam and electron beam radiation treatment plan; and determining said selection criterion on the basis of the evaluation of the acquired image data.

Aspects and embodiments presented herein are based on the realization that the identification of a proper a subset of beam types from a larger set of candidate beam types can be advantageously used when generating or otherwise creating a combined photon beam and electron beam radiation treatment plan for cancer treatment. One possible advantage is that the radiation dose to the patient can be increasingly tailor-made. In other words, it is made possible to improve dose delivery accuracy (photon vs. electron). Additionally, or alternatively, the total radiation dose may be minimized or at least reduced.

BRIEF DESCRIPTION OF DRAWINGS

These and other aspects, features and advantages will be apparent and elucidated from the following description of various embodiments, reference being made to the accompanying drawings, in which.

DETAILED DESCRIPTION

The present invention will now be described more fully hereinafter. The invention may, however, be embodied in many different forms and should not be construed as limited to the embodiments set forth herein. Rather, these embodiments are provided by way of example so that this disclosure will be thorough and complete, and will fully convey the scope of the invention to those persons skilled in the art. Like reference numbers refer to like elements or method steps throughout the description.

The aspects and embodiments disclosed herein relate to a single optimization routine which allows for optimizing, or at least improving, both photon and electron delivery in a combined photon beam and electron beam radiation treatment to be used for cancer treatment. This in turn may facilitate tumor treatment utilizing a combination of photons and electrons. Aspects and embodiments presented herein are based on the realization that the identification of a proper a subset of beam types from a larger set of candidate beam types can be advantageously used when generating the combined photon beam and electron beam radiation treatment plan. One possible advantage is that the radiation dose to the patient can be increasingly tailor-made. In other words, it is made possible to improve dose delivery accuracy (photon vs. electron). Additionally, or alternatively, the total radiation dose may be minimized or at least reduced.

In general this disclosure therefore proposes a selection of a subset of beam types out of a larger set of candidate beam types during treatment planning for combined photon-electron therapy. As a mere introduction to the following detailed description and in order to provide context to the later described aspects and embodiments of the present invention, treatment planning will first be briefly discussed. During electron and photon irradiation, the shape of the radiation field is typically controlled by one or more therapy devices (e.g. photon therapy devices and electron therapy devices). For example, the shape of the radiation field may be controlled by motorized collimating devices that are integrated in a treatment head (such as multi-leaf collimators (MLCs) and jaws) or accessory devices such as applicators or cut-outs (electrons primarily). Another type of accessory device are wedges, which may be used to control a fluence profile of the therapeutic field. The orientation of the field relative to the patient may for example be determined or otherwise established by rotations of the gantry, couch, and/or treatment head. A treatment may be administered in several fractions, and each treatment fraction may be composed of a sequence of beams. A beam may be specified as a sequence of control points, where each control point defines a given configuration of the field shaping devices and an orientation of the field at some cumulative monitor unit (MU) level. For instance, the configuration of the motorized collimating devices may change between control points, as well as the orientation of the field relative to the patient. The cumulative MU reading may be unchanged between control points to represent changes to the field shape or field orientation while the irradiation is switched off. The beam energy or even the modality could in principle be changed within one beam if this is supported by the treatment hardware, but such changes are generally not standard today. Generally speaking, it is therefore often assumed that each beam has a distinct modality (photons or electrons) and a constant beam energy. Hereinafter, the term "beam type" may be used to refer to a selected configuration of modality, beam energy, a set of accessory devices, etcetera. It should be appreciated that the description of a beam as a sequence of control points may comprise all standard delivery techniques for modulated external beam radiation therapy as special cases, i.e., step-and-shoot intensity-modulated radiation therapy (IMRT), sliding-window IMRT, volumetric-modulated arc therapy (VMAT), 3D conformal radiation therapy, or conformal arc therapy. Hybrid variants of these delivery techniques, such as hybrid IMRT-VMAT, are also included. A treatment plan for a combined photon-electron treatment may be created and evaluated in a treatment planning system (TPS), hereinafter interchangeably referred to as the radiation treatment system (see FIG. 1). The radiation treatment system may for example be configured to determine or otherwise calculate the planned dose distribution in the patient volume based on an acquired image (e.g., utilizing a computed tomography (CT) scanner). Sometimes, an intermediate step in the dose determination or computation is the calculation of energy fluence distributions for each beam based on the beam's control points. The radiation treatment system may for example optimize or otherwise generate the treatment plan with either the control points or the fluences as variables. These two types of optimization are sometimes called direct machine parameter optimization (DMPO) and fluence map optimization (FMO), respectively. Commonly, but not necessarily, a treatment plan is generated or otherwise created in two phases where FMO is followed by DMPO.

Figure 1:
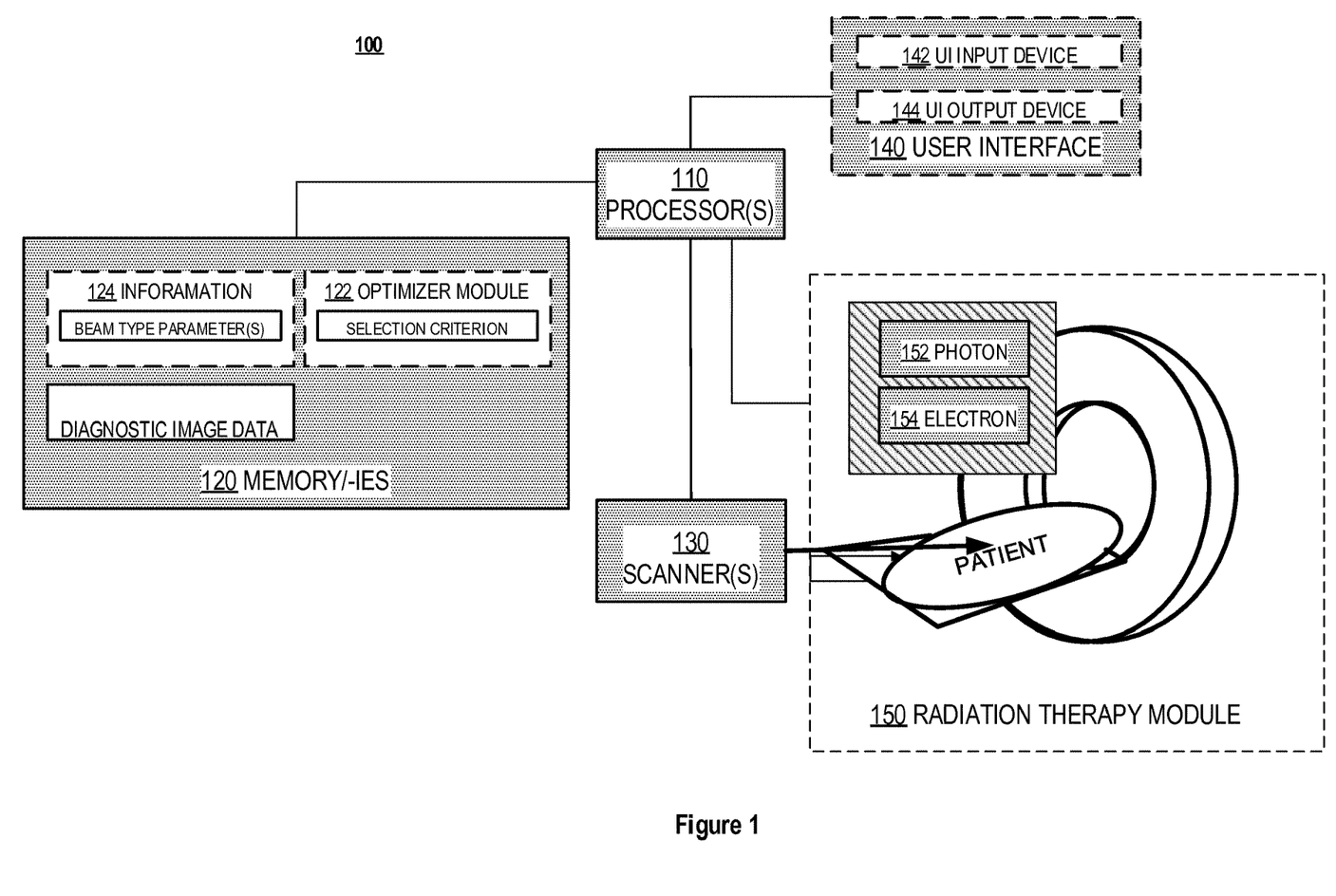
FIG. 1 schematically illustrates a radiation treatment system capable of facilitating the optimization a multimodal radiation therapy plan employing a combined photon beam and electron beam radiation treatment.

Reference will now be made to the figures, where FIG. 1 illustrates an example system 100 where aspects and embodiments of the present invention may be applied. The system 100 is sometimes referred to as a radiation treatment system. The system 100 is configured for facilitates optimization a multimodal radiation therapy plan employing a combined photon beam and electron beam radiation treatment. Accordingly, the system 100 is configured for facilitating multimodal radiotherapy optimization where the radiation therapy plan employs a combination of photon beam and electron beam radiation treatment.

In the existing art for optimization of photon and electron beam treatment, in which if a user or operator desires to combine the treatments, s/he would typically have to create a radiotherapy plan based on each modality (i.e., photon or electron) separately. Hence, s/he would be forced to optimize, or otherwise, plan the treatment for one delivery option (i.e., photon or electron) at a time. In contrast, the system illustrated in FIG. 1 facilitate using a single combined optimization technique for multimodal radiation therapy planning employing a combination of both photon beam radiation treatment and electron beam radiation treatment.

With continued reference to FIG. 1, the system 100 comprises one or several processor(s) 110 or controller(s). The processors(s) 100 is/are communicatively connected to one or several memory/-ies 120. One or more of the memories 120 may comprise instructions executable by the processor(s) 110 whereby the system 100 is operative to perform the various functions and/or methods described throughout this disclosure.

The processor(s) 110 may also be communicatively connected to a user interface (UI) 140. A user or operator (not shown) may interact with and operate the UI 140, e.g., for controlling the operation of the system 100. To this end, the UI 140 may thus comprise UI input device for receiving user input. Additionally, or alternatively, the UI 140 may comprise a UI output device for outputting information to the user. In some embodiments, the UI 140 may be implemented as a touch-sensitive UI. For example, the UI may comprise a touch-sensitive display suitably incorporating the functionalities of both a UI input device and a UI output device.

The processor(s) 110 is/are also communicatively connected to a multimodal radiation therapy module 150. Furthermore, the memory/-ies may comprise instructions executable by the processor(s) whereby the system 10 is operative to concurrently optimizing a dose delivery from a photon therapy device 152 and an electron therapy device 154 applying a generated combined photon beam and electron beam radiation treatment plan. To this end, the radiation therapy module 150 may be provided with the photon therapy device 152 and the electron therapy device 154. As is illustrated in FIG. 1, the photon therapy device 152 and the electron therapy device 154 may advantageously be implemented in one single apparatus, which then combines the photon and electron therapies. However, it should be appreciated that it is conceivable that the photon therapy device 152 and the electron therapy device 154 could alternatively be provided as separate devices.

The photon therapy device 152 and the electron therapy device 154 can be used to treat a patient using a combined or dual radiation treatment plan employing photon beam radiation as well as electron beam radiation. To this end, information 124 related to a set of candidate beam types for the combined photon beam and electron beam radiation treatment may be stored in a memory of the memory/ies 120. Each candidate beam type of the set of candidate beam types may also include, or be associated with, one or more beam type parameters. The beam type parameters may include without limitation: beam energy; beam modality; beam trajectory; dose per unit of time; distance to volume of interest; beam placement on or within volume of interest; beam modifiers such as MLC, jaws, wedges, blocks, scattering foil, compensator, cutout and bolus; and machine characteristics. Also, an optimizer module 122 may be stored in a memory of the memory/ies 120. The optimizer module 122 may include at least one selection criterion. As will be discussed later herein, a set of candidate beam types may be compared against the selection criterion to establish a subset of beam types from the candidate beam types. Advantageously, but not necessarily, the above-mentioned selection criterion imposes a requirement such that only a limited number of beam types qualify as the subset of beam types for subsequent utilization in the combined photon beam and electron beam radiation treatment plan. In addition, the optimizer module 122 may optimize, or otherwise generate, the combined photon beam and electron beam radiation treatment plan utilizing only the established subset of beam types.

In advantageous embodiments, the system 100 further includes a scanner 130. The scanner 130 may be a CT scanner or other diagnostic scanner. The scanner 130 is configured to scan the patient to acquire an image of a volume of interest to be treated using the combined photon beam and electron beam radiation treatment plan. In some embodiments, the acquired image can be converted into image data that may be stored as diagnostic image data in a memory of the memory/ies 120. The determination of the earlier-mentioned selection criterion may advantageously be made based on an evaluation of the image data, as will be discussed in some more detail hereinbelow.

In view of the above, it will be appreciated that the radiation treatment system 100 may be configured to generate the combined photon beam and electron beam radiation treatment plan utilizing only the established subset of beam types. Aspects and embodiments are based on the realization that the identification of a proper a subset of beam types from a larger set of candidate beam types can be advantageously used when generating or otherwise creating the combined photon beam and electron beam radiation treatment plan for cancer treatment. One possible advantage is that the radiation dose to the patient can be increasingly tailor-made. In other words, it is made possible to improve dose delivery accuracy (photon vs. electron). Additionally, or alternatively, the total radiation dose may be minimized or at least reduced. This may in turn lead to improved optimization and, consequently, improved cancer treatment. Due to the unique nature of the radiation treatment system 100 in FIG. 1, a user or operator is able to perform optimization of multimodal radiation therapy plans employing a combined photon beam and electron beam radiation treatment that cannot be done using conventional techniques.

As described earlier herein and despite the advances in radio therapy technology, some existing multimodal radiation therapy plans employing a combined photon beam and electron beam radiation treatment may be inadequate. To address the still unmet need of improved multimodal radiation therapy plans employing a combined photon beam and electron beam radiation treatment, and in accordance with an aspect, the present disclosure therefore also proposes a method as is schematically illustrated in the flow chart in FIG. 2.

Figure 2:
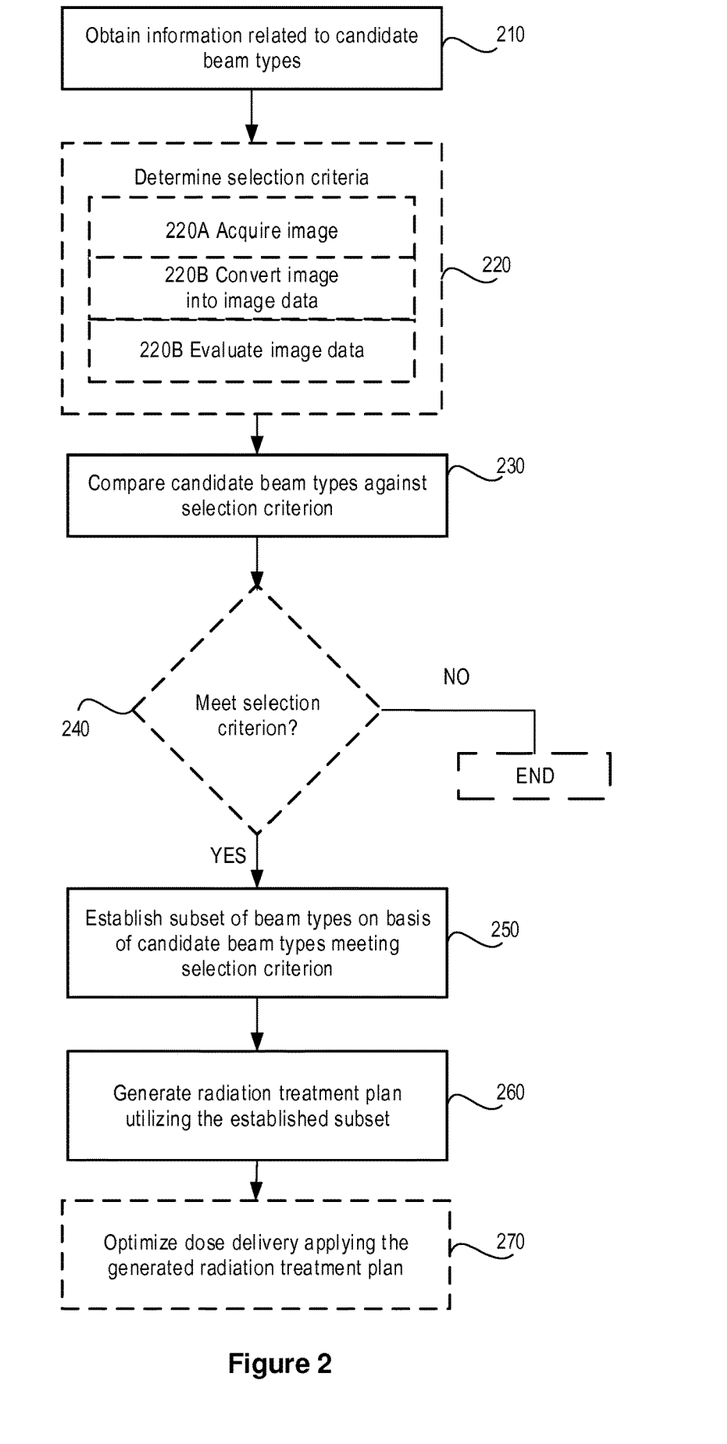
FIG. 2 schematically illustrates a flow chart of a method performed by, or implemented in, a radiation treatment system.

Accordingly, FIG. 2 schematically illustrates a flow chart of a method for facilitating optimization of a multimodal radiation therapy plan employing a combined photon beam and electron beam radiation treatment. In other words, FIG. 2 suggests a method that finds particular utility in combined photon-electron treatments of cancer.

The method is advantageously, but not necessarily, performed by or otherwise implemented in the radiation treatment system 100 shown in FIG. 1.

Action 210: Information related to a set of candidate beam types is obtained. The set of candidate beam types is typically a set of candidate beam types that are useful or otherwise finds utility in a combined photon beam and electron beam radiation treatment. Each candidate beam type of the set of candidate beam types may include one or more beam type parameters. A beam type parameter may include one or more of the following: beam energy; beam modality; beam trajectory; dose per unit of time; distance to volume of interest; beam placement on or within volume of interest; beam modifiers such as MLC, jaws, wedges, blocks, scattering foil, compensator, cutout and bolus; and machine characteristics.

Action 220: Optionally, a selection criterion may be determined or otherwise established. For example, an image may be acquired 220A. The acquired image is typically an image of a volume of interest to be treated using the combined photon beam and electron beam radiation treatment plan. This image may, for example, be acquired by a scanner. Therefore, the acquired image may sometimes be referred to as a scanned image. Based on the acquired image, image data can be formed or otherwise created. In other words, the acquired image may be converted 220B into image data. This image data thus includes data representing the image that was previously acquired. Accordingly, the image data may include data representing a scanned image. As will be appreciated, the image data therefore includes data representing the image of said volume of interest to be treated using the combined photon beam and electron beam radiation treatment plan. The image data may subsequently also be evaluated 220C and, based on this evaluation, said selection criterion can be determined 220 or otherwise established. During the evaluation, the image data may for example be segmented to identify the location, size, shape, etcetera of the targets of the patient such as tumors to be treated and/or sensitive tissue to be avoided and/or dense tissue such as bone that can adversely affect dose delivery.

Action 230: The set of candidate beam types are compared against a selection criterion to establish a subset of beam types from the candidate beam types. The selection may optionally have been determined in action 220. Alternatively, the selection criterion may be a pre-defined selection criterion. For example, the pre-defined selection criterion may be determined or otherwise established by a user, e.g. a user or operator of the system 100 illustrated in FIG. 1.

Advantageously, the selection criterion imposes a requirement such that only a limited number of beam types qualify as the subset of beam types for subsequent utilization in the combined photon beam and electron beam radiation treatment plan utilizing only the established subset of beam types.

Action 250: The subset of beam types from the candidate beam types can be established or otherwise determined based on the comparison in action 230. For example, if or when a candidate beam type meets the selection criterion this candidate beam type will be decided or otherwise be concluded to qualify for the narrower, more limited, set of beam types. As will be appreciated, and in accordance with this example embodiment, candidate beam types meeting the selection criterion would thus be selected, or otherwise determined, to represent or form the subset of beam types.

Action 260: The combined photon beam and electron beam radiation treatment plan is generated, or otherwise created or formed, utilizing only the established subset of beam types.

Action 270: Dose delivery from the photon therapy device and the electron therapy device applying the generated combined photon beam and electron beam radiation treatment plan may be optimized concurrently. For example, it may be possible to optimize or otherwise adjust coverage area, dose (photon vs. electron), and/or other delivery parameters.

As will be appreciated from the discussion above, the present disclosure thus recognizes the fact that it is possible to evaluate and test the earlier-mentioned selection criterion such that only candidate beam types with certain characteristics meeting the selection criterion represent or form the subset of beam types.

This disclosure proposes a way of facilitating optimization of a multimodal radiation therapy plan employing a combined photon beam and electron beam radiation treatment. Only utilizing a subset of proper beam types from a larger set of candidate beam types allow for improved accuracy and/or increased reliability in the subsequent generation or creation of the multimodal radiation treatment plan. Improved accuracy and/or increased reliability in turn may lead to improved optimization and, accordingly, improved cancer treatment.

Figure 3:
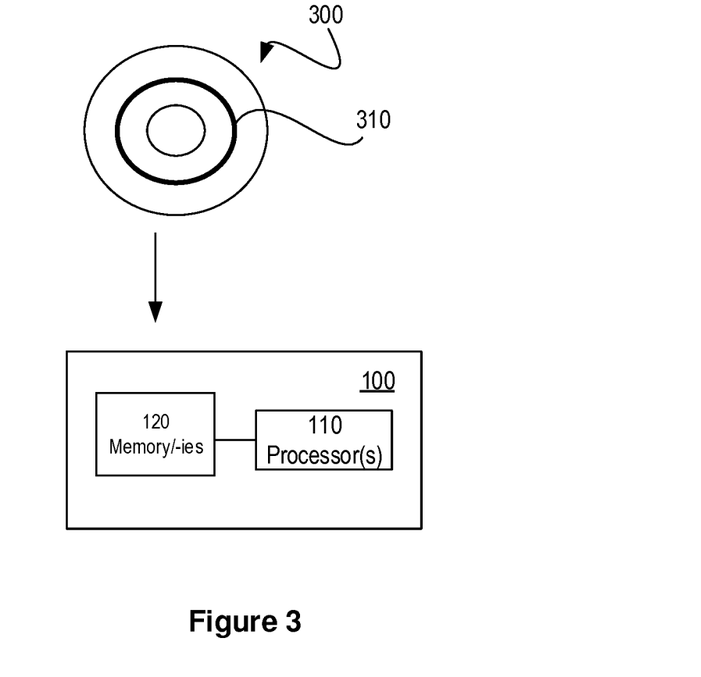
FIG. 3 schematically illustrates a carrier containing a computer program, in accordance with one aspect.

Turning now to FIG. 3, another aspect will be briefly discussed. FIG. 3 shows an example of a computer-readable medium, in this example in the form of a data disc 300. In one embodiment the data disc 300 is a magnetic data storage disc. The data disc 300 is configured to carry instructions 310 that can be loaded into a memory 120 of an apparatus, such as the system 100 illustrated in FIG. 1. Upon execution of said instructions by a processor 110 of the apparatus 100, the apparatus 100 is caused to execute a method or procedure according to any one of the methods disclosed in this disclosure, for example in conjunction with FIG. 2. The data disc 300 is arranged to be connected to or within and read by a reading device (not shown), for loading the instructions into the processor 110. One such example of a reading device in combination with one (or several) data disc(s) 300 is a hard drive. It should be noted that the computer-readable medium can also be other mediums such as compact discs, digital video discs, flash memories or other memory technologies commonly used. In such an embodiment the data disc 300 is one type of a tangible computer-readable medium. The instructions may alternatively be downloaded to a computer data reading device, such as a computer or other apparatus 100 capable of reading computer coded data on a computer-readable medium, by comprising the instructions in a computer-readable signal (not shown) which is transmitted via a wireless (or wired) interface (for example via the Internet) to the computer data reading device for loading the instructions into a processor 110 of the apparatus 100. In such an embodiment, the computer-readable signal is one type of a non-tangible computer-readable medium.

Various Detailed Optimization Examples

As is appreciated from the aspects and embodiments described hitherto in this disclosure, the he combined photon beam and electron beam radiation treatment plan is advantageously generated or otherwise created by utilizing only the established subset of beam types. This disclosure thus proposes a way of facilitating optimization of a multimodal radiation therapy plan employing a combined photon beam and electron beam radiation treatment. Only utilizing a subset of proper beam types from a larger set of candidate beam types allow for improved accuracy and/or increased reliability in the subsequent generation or creation of the multimodal radiation treatment plan. Improved accuracy and/or increased reliability in turn may lead to improved optimization and, accordingly, improved cancer treatment.

In the following, certain examples of the treatment plan optimization will be discussed in some more detail. The treatment plan optimization may, however, be reduced to practice in many different forms and should not be construed as limited to the examples set forth herein. Rather, these examples are provided by way of example so that this disclosure will be increasingly thorough and complete to those persons skilled in the art.

In accordance with some aspects, the treatment plan optimization may be formulated as a mathematical problem according to the following:

$$\text{minimize } f(x)$$

$$\text{subject to } c_j(x) \leq 0, j=1,\ldots,m, \quad (1)$$

where the vector of optimization variables x represents the beam parameters that are to be optimized, the objective function f is a measure of plan quality defined such that lower values are typically better, and the constraint functions $c_1, \ldots, c_m$ are functions that represent non-negotiable requirements on the optimized plan. The constraint functions may be defined such that a requirement is fulfilled if the function value is non-positive.

The vector x is the concatenation of all optimization variables of each beam type into a single vector, e.g. according to the following:

$$x = \begin{pmatrix} x^{(1)} \\ \vdots \\ x^{(B)} \end{pmatrix}, \quad (1)$$

where each sub-vector $x^{(b)}$ defines the optimization variables for the b:th beam type. As an example, a vector $x^{(b)}$ is during the DMPO phase typically the concatenation of the vector $\lambda^{(b)}$ of MLC leaf positions across all control points of beam type b and the vector $\mu^{(b)}$ of MUs across all control points of beam type b, e.g., $$x^{(b)} = \begin{pmatrix} \lambda^{(b)} \\ \mu^{(b)} \end{pmatrix}.$$

A vector $x^{(b)}$ is similarly the concatenation of bixel fluences of beam type b during the FMO phase. A bixel associated with some beam is generally a surface element in a plane perpendicular to the beam central axis.

The vector of variables x may also include elements that represent other types of treatment plan parameters, such as parameters that control the orientation of the beams relative to the patient.

An objective function f may be a sum of terms according to the following:

$$f(x) = \sum_{i=1}^{n} f_i(x),$$

where each constituent function $f_i$ measures some aspect of treatment plan quality with respect to a given sub-region of the patient volume. A constituent $f_i$ may, e.g., penalize deviation from the prescribed dose of a target structure, or penalize dose in excess of some tolerance level for a healthy organ, etcetera. Typical constraint functions $c_i$ are either functions that impose requirements on the planned dose—such as an upper limit on the dose to a healthy organ or a lower limit on the dose to a target structure or, alternatively, functions that reflect some physical or mechanical limitation of the delivery method. Examples of the latter type of constraint are non-negativity constraints on the bixel intensities or control point MUs, constraints that impose boundaries on the MLC leaf positions, and constraints that e.g. prohibit overlap between two opposed MLC leaves. As will be appreciated, this is just an example and the optimization problem could be formulated differently, e.g., the machine constraints could be included in the objective function.

Problem Formulation

The present disclosure recognizes an unmet need to control the complexity of a photon-electron treatment plan by imposing limits on the number of different beam types that are part of the treatment plan. Such a limitation may be expressed as using a constraint function $c_j$ for a problem according to (1) where x represents the parameters of a set of candidate beam types. The complexity-limiting constraint function $c_j$ may be formulated mathematically by the introduction of a function $y_b$ for each candidate beam type, defined such that $y_b(x^{(b)})$ is positive if the b:th candidate beam type is selected, and zero otherwise. An example of a valid definition of $y_b$ during DMPO can be some norm of the control point MUs associated with beam type b, e.g., $$y_b(x^{(b)}) = \|\mu^{(b)}\|_2 = \sqrt{\sum_i |\mu_i|^2}, \quad (2)$$

if the Euclidean norm is used. The function $y_b$ may be defined similarly with respect to the beamlet intensities during FMO.

The functions $y_1, \ldots, y_B$ may allow a constraint function $c_j$ that imposes an upper bound $B^{max}$ on the number of selected beam types to be formulated according to the following:

$$c_j(x) = \sum_{b=1}^{B} \theta(y_b(x^{(b)})) - B^{max} \quad (3)$$

where $\theta$ is the step function $$\theta(z) = \begin{cases} 0 & \text{if } z \le 0 \\ 1 & \text{otherwise} \end{cases}. \quad (4)$$

It should be appreciated that $B^{max}$ should be less than the number of available beam types B to influence the optimization. Similar constraints may also be defined with respect to a subset of beam types, e.g., $$c_j(x) = \sum_{b \in I} \theta(y_b(x^{(b)})) - B^{max}$$

where l is some subset of $\{1, \ldots, B\}$.

The complexity-limiting constraint (3) may be relaxed into a penalty term in the objective function according to, e.g.:

$$f_i(x) = \max\{c_j(x), 0\}^2, \quad (5)$$

where the penalty may be defined to increase quadratically with the magnitude of the constraint violation.

Algorithm Examples

Figure 4:
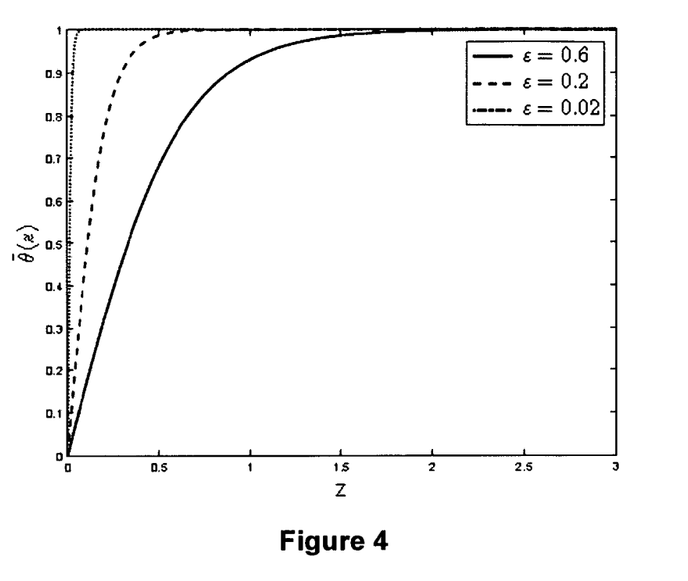
FIG. 4 illustrates an approximate step function for different smoothing parameters.
Figure 5:
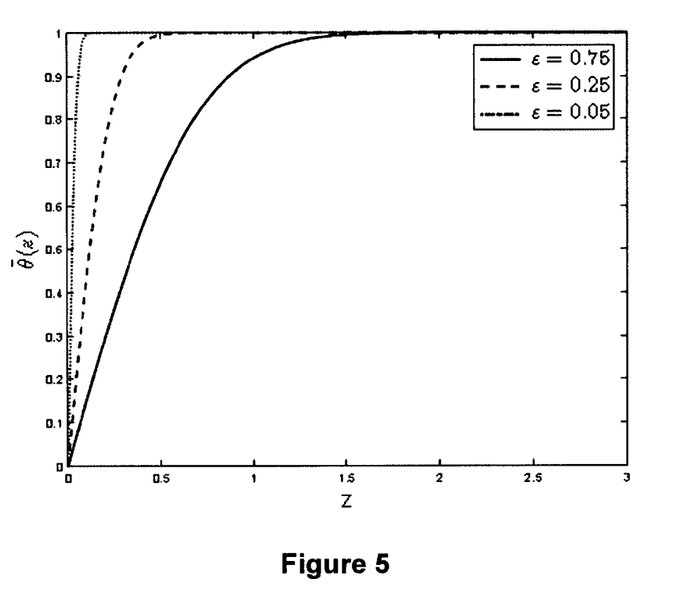
FIG. 5 illustrates another approximate step function for different smoothing parameters.

Relaxation to a Continuous Optimization Problem:
A complexity-limiting constraint (3) or penalty (5) may not be suitable for optimization because the step function (4) is discontinuous. A remedy for this difficulty may be to substitute a smooth but approximate step function $\tilde{\theta}$ for the exact step function $\theta$. An example of an approximate step function that could be suitable for optimization is the hyperbolic tangent, i.e.:

$$\tilde{\theta} = \tanh\left(\frac{z}{\varepsilon}\right) = \frac{e^{2z/\varepsilon} - 1}{e^{2z/\varepsilon} + 1} \quad (6)$$

where the positive scalar E controls how close $\tilde{\theta}$ is to $\theta$, see FIG. 4. Another example is the error function, i.e.:

$$\tilde{\theta}(z) = \text{erf}(z/\varepsilon) = \frac{2}{\sqrt{\pi}} \int_0^{z/\varepsilon} e^{-t^2} dt, \quad (7)$$

see FIG. 5.

The reformulation of (3) or (5) into a smooth continuous function may advantageously transform the optimization problem (1) to a continuous non-linear problem. Several different well-known methods may be used to solve such a problem, for example, gradient-based optimization methods such as interior point methods or sequential quadratic programming methods, or derivative-free optimization methods such as simulated annealing methods or genetic algorithms.

Optimization with respect to a smoothed step function $\theta$ does not always produce a solution x that satisfies the original requirement $c_j(x) \leq 0$ precisely. A sub-routine that converts a mildly infeasible solution to feasible ones can therefore sometimes be beneficial. If the functions $y_1, \ldots, y_B$ satisfy $y_b(0)=0$ for all b, which is the case for the example according to (2), then it is possible to counteract infeasibility by sorting $y_1(x^{(1)}), \ldots, y_B(x^{(B)})$ in ascending order to obtain a sequence of indices $i_1, \ldots, i_B$. The vectors $x^{(i1)}, \ldots, x^{(iB)}$ may then be truncated to zero one at a time until feasibility is obtained. It should be appreciated that this procedure may be used to make a solution feasible with respect to some intermediate upper bound $\tilde{b}$ that is larger than the desired maximum number of beam types $B^{max}$.

The smooth formulation of the complexity-limiting constraint and the infeasibility correction routine may be combined into the following algorithm for selecting at most $B^{max}$ beam types out of B possible candidates:
1. Select some initial x, $\varepsilon$, and $\tilde{b}$
2. Optimize with respect to (1) using some nonlinear optimization method
3. Make the optimized solution x feasible with respect to the constraint $c_{jl\ (x) \leq \tilde{b} - B}^{max}$
4. Update $\varepsilon$ and $\tilde{b}$
5. Repeat actions or steps 2-4 until some termination criterion is met.

Examples of termination criteria that could be used is that feasibility with respect to the maximum number of allowed beam types $B^{max}$ has been obtained or that a maximum number of iterations has been performed.

Algorithms for minimizing a smooth penalty according to (5) may be constructed in similar fashion.

Exhaustive Enumeration:

It may be computationally feasible to select the optimal subset of beam types by exhaustive enumeration if the number of candidate beam types B or the maximum number of allowed beam types $B^{max}$ is small or relatively small. For example, if a single photon energy is to be used, no accessory devices need to be selected, and the treatment machine supports seven electron energies out of which two should be selected, then there are $$\binom{7}{2} = 21$$

different feasible pairs of electron energies.

The corresponding 21 different instances of (1) where some pair of electron energies are selected and the variables corresponding to the remaining electron energies are discarded may be solved independently. The optimized solutions can finally be compared to identify the optimal pair of electron energies. The different problem instances may preferably be solved in parallel.

Greedy Heuristics:

The algorithm outlined in the section "Relaxation to a continuous optimization problem" may be simplified to a reverse-greedy algorithm that begins with all possible beam types and sequentially discards the beam type that makes the smallest contribution to the current solution x. This simplification may be obtained if the complexity-limiting constraint is not taken into consideration at the optimization step (Step 2 above under the section "Relaxation to a continuous optimization problem").

Beam types may also be selected using a forward-greedy algorithm that starts with an empty set of selected beam types and iteratively adds types based on which beam type that improves the current solution the most. The best not yet selected beam type can be identified by exhaustive enumeration.

As will be appreciated from the examples described herein, the present disclosure is based on the notion that there is still an unmet need for facilitating optimization of a multimodal radiation therapy plan employing a combined photon beam and electron beam radiation treatment. The present disclosure proposes a treatment plan optimization for a combined photon-electron treatment where at least one complexity requirement related to one or more beam type parameters selected for the treatment is taken into consideration. "Complexity" in this regard should be understood as relating to the number of different types of beams that are used, with a beam type being a selection of the treatment energy, scattering foil and/or bolus, etc. as explained throughout this disclosure. A low plan complexity may be desirable because changes of the beam energy, scattering foils and/or bolus could be time consuming. A complexity requirement could, for example, limit the number of different beam types that are used for treatment. The disclosure has therefore focuses on complexity requirements formulated as constraints on the total number of beam types. More sophisticated measures could also be used. The different beam types could for example be assigned with different time costs and the overall sum of time costs taken into consideration. Multiple complexity requirements could also be used in parallel, such as constraints on the total number of beam energies in combination with constraints on the number of individual photon and/or electron energies. A constraint on the maximum number of selected energies can be relaxed into a penalty term in the objective function of the optimization formulation. Minimization of the number of selected energies instead of an explicit constraint can be useful to control the tradeoff between plan quality and number of energies. A treatment plan that uses all or substantially all possible energies could for instance first be created, and a second optimization problem then solved where the number of selected energies is minimized subject to constraints that prevent too large changes to the planned dose distribution. Selection of a subset of beam types from a larger set of candidate beam types in combination with optimization of the photon and electron control points may lead to a mixed-integer optimization problem.

The present disclosure has proposed a treatment plan optimization for a combined photon-electron treatment where at least one complexity requirement related to one or more beam type parameters selected for the treatment is taken into consideration. The beam type parameters may for example be related to one or several of the following: beam energy; beam modality; beam trajectory; dose per unit of time; distance to volume of interest; beam placement on or within volume of interest; beam modifiers such as MLC, jaws, wedges, blocks, scattering foil, compensator, cutout and bolus; and machine characteristics. An advantage with the examples described throughout this disclosure is that the photon and electron components of the combined photon-electron treatment may be optimized concurrently.

Aspects and embodiments presented herein are based on the realization that the identification of a proper a subset of beam types from a larger set of candidate beam types can be advantageously used when generating or otherwise creating a combined photon beam and electron beam radiation treatment plan for cancer treatment. One possible advantage is that the radiation dose to the patient can be increasingly tailor-made. In other words, it is made possible to improve dose delivery accuracy (photon vs. electron). Additionally, or alternatively, the total radiation dose may be minimized or at least reduced. This may in turn lead to improved optimization and, consequently, improved cancer treatment.

In the detailed description hereinabove, for purposes of explanation and not limitation, specific details are set forth in order to provide a thorough understanding of various aspects and embodiments described in this disclosure. In some instances, detailed descriptions of well-known devices, components, circuits, and methods have been omitted so as not to obscure the description of the embodiments disclosed herein with unnecessary detail. All statements herein reciting principles, aspects, and embodiments disclosed herein, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure. Thus, for example, it will be appreciated that block diagrams herein can represent conceptual views of illustrative circuitry or other functional units embodying the principles of the described embodiments. Similarly, it will be appreciated that any flow charts and the like represent various processes which may be substantially represented in computer readable medium and so executed by a computer or processor, whether or not such computer or processor is explicitly shown. The functions of the various elements including functional blocks, may be provided through the use of hardware such as circuit hardware and/or hardware capable of executing software in the form of coded instructions stored on the above-mentioned computer readable medium. Thus, such functions and illustrated functional blocks are to be understood as being either hardware-implemented and/or computer-implemented, and thus machine-implemented. In terms of hardware implementation, the functional blocks may include or encompass, without limitation, digital signal processor (DSP) hardware, reduced instruction set processor, hardware (e.g., digital or analog) circuitry including but not limited to application specific integrated circuit(s) [ASIC], and/or field programmable gate array(s) (FPGA(s)), and (where appropriate) state machines capable of performing such functions. In terms of computer implementation, a computer is generally understood to comprise one or more processors or one or more controllers. When provided by a computer or processor or controller, the functions may be provided by a single dedicated computer or processor or controller, by a single shared computer or processor or controller, or by a plurality of individual computers or processors or controllers, some of which may be shared or distributed. Moreover, use of the term "processor" or "controller" may also be construed to refer to other hardware capable of performing such functions and/or executing software, such as the example hardware recited above.

Modifications and other variants of the described embodiments will come to mind to one skilled in the art having benefit of the teachings presented in the foregoing description and associated drawings. Therefore, it is to be understood that the embodiments are not limited to the specific example embodiments described in this disclosure and that modifications and other variants are intended to be included within the scope of this disclosure. Furthermore, although specific terms may be employed herein, they are used in a generic and descriptive sense only and not for purposes of limitation. Therefore, a person skilled in the art would recognize numerous variations to the described embodiments that would still fall within the scope of the appended claims. As used herein, the terms "comprise/comprises" or "include/includes" do not exclude the presence of other elements or steps. Furthermore, although individual features may be included in different claims, these may possibly advantageously be combined, and the inclusion of different claims does not imply that a combination of features is not feasible and/or advantageous. In addition, singular references do not exclude a plurality.

The invention claimed is:

1. A method of facilitating optimization of a multimodal radiation therapy plan employing a combined photon beam and electron beam radiation treatment, the method being performed by a radiation treatment system and comprising:
    obtaining information related to a set of candidate beam types for the combined photon beam and electron beam radiation treatment, each candidate beam type of the set of candidate beam types including one or more beam type parameters;
    comparing the set of candidate beam types against a selection criterion to establish a subset of beam types from the candidate beam types, wherein the selection criterion imposes a requirement such that only a limited number of beam types qualify as the subset of beam types for subsequent utilization in the combined photon beam and electron beam radiation treatment plan;
    generating the combined photon beam and electron beam radiation treatment plan utilizing only the established subset of beam types; and
    concurrently optimizing a dose delivery from a photon therapy device and an electron therapy device applying the generated combined photon beam and electron beam radiation treatment plan.

2. The method according to claim 1, wherein a beam type parameter includes one or more of: beam energy; beam modality; beam trajectory; dose per unit of time; distance to volume of interest; beam placement on or within volume of interest; beam modifiers including one or more of: multileaf collimator, jaws, wedges, blocks, scattering foil, compensator, cutout and bolus; and machine characteristics.

3. The method according to claim 1, comprising:
    acquiring an image, by means of a scanner, of a volume of interest to be treated using the combined photon beam and electron beam radiation treatment plan;
    converting the acquired image into image data;
    evaluating the image data; and
    determining said selection criterion on the basis of the evaluation of the image data.

4. A radiation treatment system that facilitates optimization a multimodal radiation therapy plan employing a combined photon beam and electron beam radiation treatment, the radiation treatment system comprising:
    at least one processor; and
    at least one memory comprising instructions executable by the at least one processor whereby the radiation treatment system is operative to:
        obtain information related to a set of candidate beam types for the combined photon beam and electron beam radiation treatment, each candidate beam type of the set of candidate beam types including one or more beam type parameters;

compare the set of candidate beam types against a selection criterion to establish a subset of beam types from the candidate beam types, wherein the selection criterion imposes a requirement such that only a limited number of beam types qualify as the subset of beam types for subsequent utilization in the combined photon beam and electron beam radiation treatment plan;

generate the combined photon beam and electron beam radiation treatment plan utilizing only the established subset of beam types; and concurrently optimize a dose delivery from a photon therapy device and an electron therapy device applying the generated combined photon beam and electron beam radiation treatment plan.

5. The radiation treatment system according to claim 4, wherein a beam type parameter includes one or more of: beam modality; beam trajectory; dose per unit of time; distance to volume of interest; beam placement on or within volume of interest; beam modifiers including one or more of: multileaf collimator, jaws, wedges, blocks, scattering foil, compensator, cutout and bolus; and machine characteristics.

6. The radiation treatment system according to claim 4, wherein the at least one memory comprises instructions executable by the at least one processor whereby the radiation treatment system is operative to:

acquire, by means of a scanner, an image of a volume of interest to be treated using the combined photon beam and electron beam radiation treatment plan;

convert the acquired image into image data;

evaluate the image data; and determine said selection criterion on the basis of the evaluation of the image data.

7. A non-transitory computer-readable medium having stored thereon one or more sequences of instructions for causing one or more processors to perform:

obtaining information related to a set of candidate beam types for the combined photon beam and electron beam radiation treatment, each candidate beam type of the set of candidate beam types including one or more beam type parameters;

comparing the set of candidate beam types against a selection criterion to establish a subset of beam types from the candidate beam types, wherein the selection criterion imposes a requirement such that only a limited number of beam types qualify as the subset of beam types for subsequent utilization in the combined photon beam and electron beam radiation treatment plan;

generating the combined photon beam and electron beam radiation treatment plan utilizing only the established subset of beam types; and concurrently optimizing a dose delivery from a photon therapy device and an electron therapy device applying the generated combined photon beam and electron beam radiation treatment plan.

8. The non-transitory computer-readable medium according to claim 7, wherein a beam type parameter includes one or more of: beam modality; beam trajectory; dose per unit of time; distance to volume of interest; beam placement on or within volume of interest; beam modifiers including one or more of: multileaf collimator, jaws, wedges, blocks, scattering foil, compensator, cutout and bolus; and machine characteristics.

9. The non-transitory computer-readable medium according to claim 7, having stored thereon one or more sequences of instructions for causing one or more processors to perform:

evaluating image data representing an acquired image of a volume of interest to be treated using the combined photon beam and electron beam radiation treatment plan; and determining said selection criterion on the basis of the evaluation of the acquired image data.

\* \* \* \* \*